US00PP33809P2

(12) United States Plant Patent
Yamada

(10) Patent No.: US PP33,809 P2
(45) Date of Patent: Jan. 4, 2022

(54) ***CATHARANTHUS* PLANT NAMED 'SUNCATH 132'**

(50) Latin Name: *Catharanthus roseus*
Varietal Denomination: Suncath 132

(71) Applicant: Masahiro Yamada, Shiga (JP)

(72) Inventor: Masahiro Yamada, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 17/171,316

(22) Filed: Feb. 9, 2021

(51) Int. Cl.
*A01H 5/02* (2018.01)
*A01H 6/08* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Catharanthus* plant named 'Suncath 132', characterized by its upright to outwardly spreading and uniformly mounding plant habit; vigorous growth habit; freely basal branching habit; freely flowering habit; long flowering period; relatively small star-shaped purplish red-colored flowers with white-colored centers; and good garden performance.

2 Drawing Sheets

Figure 1:
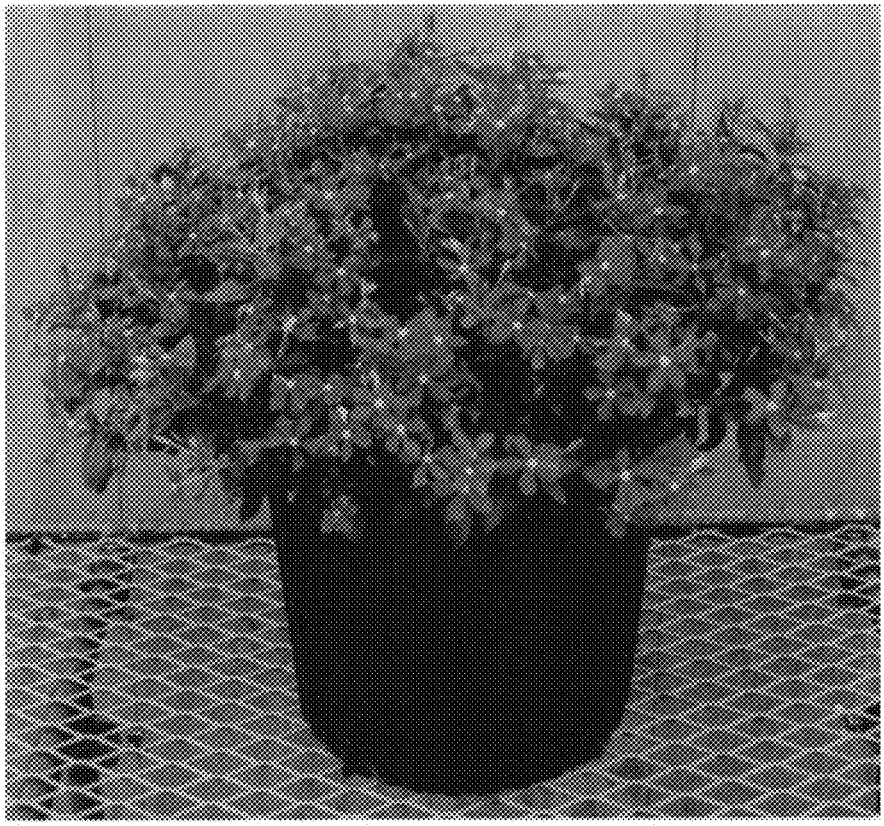

Botanical designation: *Catharanthus roseus.*
Cultivar denomination: 'SUNCATH 132'.

STATEMENT REGARDING PRIOR DISCLOSURES BY THE INVENTOR/APPLICANT & ASSIGNEE

The Inventor/Applicant and Assignee, Suntory Flowers Limited of Tokyo, Japan, assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Catharanthus* plant, botanically known as *Catharanthus roseus* and hereinafter referred to by the cultivar name 'Suncath 132'.

The new *Catharanthus* plant is a product of a planned breeding program conducted by the Inventor in Higashiomi, Shiga, Japan. The objective of the breeding program is to develop new uniform and freely branching *Catharanthus* plants with numerous small attractive flowers.

The new *Catharanthus* plant originated from a cross-pollination conducted by the Inventor in Higashiomi, Shiga, Japan in September, 2011 of a proprietary selection of *Catharanthus roseus* identified as code designation FS22-9, not patented, as the female, or seed, parent with a proprietary selection of *Catharanthus roseus* identified as code designation CL, not patented, as the male, or pollen, parent. The new *Catharanthus* plant was discovered and selected by the Inventor as a single flowering plant from within the progeny of the stated cross-pollination in a controlled greenhouse environment in Higashiomi, Shiga, Japan in September, 2013.

Asexual reproduction of the new *Catharanthus* plant by vegetative tip cuttings in a controlled greenhouse environment in Higashiomi, Shiga, Japan since December, 2013, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncath 132'. These characteristics in combination distinguish 'Suncath 132' as a new and distinct *Catharanthus* plant:

1. Upright to outwardly spreading and uniformly mounding plant habit.
2. Vigorous growth habit.
3. Freely basal branching habit.
4. Freely flowering habit.
5. Long flowering period.
6. Relatively small star-shaped purplish red-colored flowers with white-colored centers.
7. Good garden performance.

Plants of the new *Catharanthus* can be compared to plants of the female parent selection. Plants of the new *Catharanthus* differ primarily from plants of the female parent selection in the following characteristics:

1. Plants of the new *Catharanthus* have smaller flowers than plants of the female parent selection.
2. Plants of the new *Catharanthus* have purplish red-colored flowers whereas plants of the female parent selection have red-colored flowers.

Plants of the new *Catharanthus* can be compared to plants of the male parent selection. Plants of the new *Catharanthus* differ primarily from plants of the male parent selection in the following characteristics:

1. Plants of the new *Catharanthus* have smaller flowers than plants of the male parent selection.
2. Plants of the new *Catharanthus* have purplish red-colored flowers whereas plants of the male parent selection have lavender pink-colored flowers.

Plants of the new *Catharanthus* can be compared to plants of the *Catharanthus roseus* 'Suncatha 2460', disclosed in U.S. Plant Pat. No. 27,455. In side-by-side comparisons, plants of the new *Catharanthus* differ from plants of 'Suncatha 2460' in the following characteristics:

1. Plants of the new *Catharanthus* are not as broad as plants of 'Suncatha 2460'.
2. Plants of the new *Catharanthus* have larger flower petals than plants of 'Suncatha 2460'.
3. Plants of the new *Catharanthus* and 'Suncatha 2460' differ in flower color as plants of the new *Catharanthus* have purplish red-colored flowers whereas plants of 'Suncatha 2460' have light red purple-colored flowers.
4. Flowers of plants of the new *Catharanthus* have a larger "eye zone" than flowers of plants of 'Suncatha 2460'.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph on the first sheet (FIG. 1) is a side perspective view of a typical flowering plant of 'Suncath 132' grown in a container.

Figure 2:
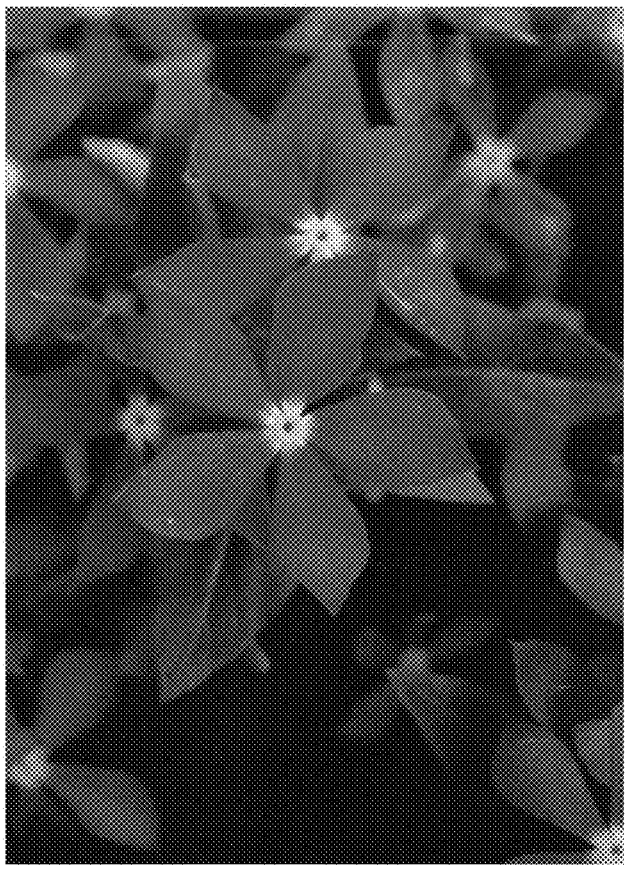

The photograph on the second sheet (FIG. 2) is a close-up view of a typical flowering plant of 'Suncath 132'.

DETAILED BOTANICAL DESCRIPTION

The aforementioned photographs and following observations, measurements and values describe plants grown during the summer in 24-cm containers in an outdoor nursery in Higashiomi, Shiga, Japan and under cultural practices typical of commercial production. During the production of the plants, day temperatures averaged 25° C. and night temperatures averaged 15° C. Plants were four months old when the photographs were taken and five months old when the description was taken. In the following description, color references are made to The Royal Horticultural Society Colour Chart, 2007 Edition, except where general terms of ordinary dictionary significance are used.

Botanical classification: *Catharanthus roseus* 'Suncath 132'.

Parentage:

*Female, or seed, parent*.—Proprietary selection of *Catharanthus roseus* identified as code designation FS22-9, not patented.

*Male, or pollen, parent*.—Proprietary selection of *Catharanthus roseus* identified as code designation CL, not patented.

Propagation:

*Type*.—By vegetative tip cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and uniformly mounding plant habit; freely basal branching habit, about ten basal branches each with about seven secondary branches developing per plant; vigorous growth habit.

*Plant height*.—About 23 cm.

*Plant diameter*.—About 45 cm.

Lateral branch description:

*Length*.—About 19.4 cm.

*Diameter*.—About 4 mm.

*Internode length*.—About 8 mm.

*Strength*.—Strong.

*Aspect*.—Upright to outwardly.

*Texture*.—Sparsely pubescent.

*Color*.—Close to 144D.

Leaf description:

*Arrangement*.—Opposite, simple.

*Length*.—About 2.9 cm.

*Width*.—About 1.4 cm.

*Shape*.—Oblong.

*Apex*.—Acute.

*Base*.—Attenuate.

*Margin*.—Entire.

*Texture, upper and lower surfaces*.—Pubescent.

*Venation pattern*.—Pinnate; reticulate.

*Color*.—Developing leaves, upper surface: Close to 137C. Developing leaves, lower surface: Close to 144A. Fully expanded leaves, upper surface: Close to 137A; venation, close to N144D. Fully expanded leaves, lower surface: Close to 138A; venation, close to 145C.

*Petioles*.—Length: About 3.1 mm. Diameter: About 1.1 mm. Texture, upper and lower surfaces: Pubescent. Color, upper and lower surfaces: Close to 145C.

Flower description:

*Flower arrangement and habit*.—Single star-shaped salverform flowers arising from upper leaf axils; freely flowering habit with about twelve flowers per lateral branch; flowers face mostly upright to slightly outwardly.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower buds*.—Length: About 2.8 cm. Diameter: About 3.3 mm. Shape: Ovoid to cylindrical. Color: Close to 64B; towards the base, close to 150D.

*Flower diameter*.—About 3 cm.

*Flower length* (*depth*).—About 2.3 cm.

*Tube length*.—About 1.9 cm.

*Tube diameter, proximally*.—About 1.1 mm.

*Tube diameter, distally*.—About 1.7 mm.

*Corolla*.—Arrangement: Five petals in a single whorl fused at the base into a tube. Petal length from throat: About 1.5 cm. Petal width: About 7.7 mm. Petal eye zone diameter: About 3.8 mm. Petal shape: Narrowly elliptic to oblanceolate. Petal apex: Cuspidate. Petal base: Fused to corolla tube. Petal margin: Entire; slightly to not undulate. Petal texture, upper and lower surfaces: Smooth, glabrous. Throat texture: Pubescent. Tube texture: Pubescent. Color: Petal, when opening, upper surface: Close to 67A. Petal, when opening, lower surface: Close to 67C; towards the tube, close to 69C. Petal, fully opened, upper surface: Close to 67A; color becoming closer to N66C with development; eye zone, close to NN155D. Petal, fully opened, lower surface: Close to N66C; towards the tube, close to 69C. Throat: Close to 144B. Tube: Close to 145C.

*Calyx*.—Arrangement: Star-shaped tubular calyx with five sepals fused towards the base. Sepal length: About 2 mm. Sepal width: About 1 mm. Sepal shape: Deltoid. Sepal apex: Acute. Sepal margin: Entire. Sepal texture, upper and lower surfaces: Sparsely pubescent. Color, upper and lower surfaces: Close to 144A.

*Peduncles*.—Length: About 1.5 mm. Diameter: About 1.1 mm. Angle: Upright to outwardly. Strength: Strong. Texture: Sparsely pubescent. Color: Close to 144B.

*Reproductive organs*.—Stamens: Quantity per flower: Five; filaments fuse to the corolla tube. Anther size: About 0.8 mm by 1.5 mm. Anther shape: Narrowly elliptic. Anther color: Close to 154D. Pollen amount: Scarce. Pollen color: Close to 158D. Pistils: Quantity per flower: One. Pistil length: About 1.8 cm. Style color: Close to 145D. Stigma shape: Globose. Stigma color: Close to 144A. Ovary color: Close to 145A. Seeds and fruits: To date, seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: To date, plants of the new *Catharanthus* have not been observed to be resistant to pathogens and pests common to *Catharanthus* plants.

It is claimed:

1. A new and distinct *Catharanthus* plant named 'Suncath 132' as illustrated and described.

* * * * *